United States Patent [19]

Curutcharry

[11] 4,406,657

[45] Sep. 27, 1983

[54] NOISE-ATTENUATING DEVICE FOR COLOSTOMY

[75] Inventor: Jean Curutcharry, Guethary, France

[73] Assignee: Laboratoires Biotrol S.A., France

[21] Appl. No.: 250,628

[22] Filed: Apr. 3, 1981

[30] Foreign Application Priority Data

Apr. 4, 1980 [FR] France ................. 80 07774

[51] Int. Cl.³ ............................... A61F 5/44
[52] U.S. Cl. ................................... 604/328
[58] Field of Search ............ 128/1 R, 283, 272; 3/1; 604/328, 332–343

[56] References Cited

U.S. PATENT DOCUMENTS

| | | | |
|---|---|---|---|
| 4,137,918 | 2/1979 | Bogert | 128/283 |
| 4,182,335 | 1/1980 | Matrulo | 128/283 |
| 4,209,009 | 6/1980 | Hennig | 128/283 |
| 4,210,132 | 7/1980 | Perlin | 128/283 |
| 4,258,704 | 3/1981 | Hill | 128/283 |

FOREIGN PATENT DOCUMENTS 2811383  9/1979  Fed. Rep. of Germany ...... 128/283

Primary Examiner—Richard J. Apley
Assistant Examiner—T. J. Wallin
Attorney, Agent, or Firm—Berman, Aisenberg & Platt

[57] ABSTRACT

A device reducing noise resulting from the emission of intestinal gas by persons who have undergone enterostomy.

Basically, it comprises an oblong body made of an open-cell porous material and/or optionally provided with an absorbent material, such as activated charcoal, and sheathed in a casing made of a material that does ot adhere to the stoma walls, and the upstream and downstream portions of which each comprises at least one opening suited to allow passage of the intestinal gases emitted, and which can be connected to a collecting bag, or secured to the stoma of persons practising irrigation.

Application to improving the comfort and the social rehabilitation of persons who have undergone enterostomy.

9 Claims, 4 Drawing Figures

NOISE-ATTENUATING DEVICE FOR COLOSTOMY

This invention relates to the abolishment or the reduction of noise emitted from an artificial anus.

Patients who have undergone enterostomy, particularly those who have undergone colostomy and ileostomy, have an intestinal opening emerging through the abdominal wall. The evacuation of intestinal residues usually cannot be controlled by these patients.

Generally speaking, the excreta is collected in plastic bags, which are secured to the patient's abdomen by adhesives or by joints, usually made of natural or synthetic paste, used with a belt system.

Such bag systems are effective for the collection of solids or liquids under acceptable conditions, but they are ineffective with respect to the intestinal gases emitted by the intestinal system.

Persons who have undergone enterostomy and who practise colonic irrigation are faced with the same problem, particularly on the second day after the enema.

These emissions of intestinal gas are unpredictable and uncontrollable and are usually accompanied by noise when they pass through the stoma.

The resulting situation constitutes a considerable embarassment for persons who have undergone enterostomy, and is prejudicial to their social rehabilitation.

Systems for the discharge and the deodorization of the intestinal gases emitted by persons who have undergone enterostomy have already been described. For some time past, various systems of filters, adhesively attached or bonded to the collecting bags for persons who have undergone enterostomy, have been proposed for this purpose (see particularly French patent application No. 77,00132 published under No. 2,337,545); but, owing to their design, they cannot contribute to abolishing the audible sounds emitted by an artificial anus, and it is obvious that they were not designed with this aim in view.

In another connection, plugging systems, notably magnetic systems, have been proposed; they provide a certain degree of lowering of the noise made by a stoma on and/or in which such a plugging system is inserted (in this connection see, among others, French patent applications No. 78,04959 and 78,16315, published under No. 2,417,291 and 2,410,999, respectively, and U.S. Pat. No. 2,931,353). But these plugging devices can only be used instead of the aforesaid collecting bags by those persons (having undergone enterostomy) who irrigate their systems and/or whose stools are very well controlled, or regular. This is only the case with a minority of patients.

It follows that thus far no solution has been proposed for the problem of noise emitted by a stoma for those persons provided with a stoma who use collecting bags. Nevertheless, this type of patient accounts for the great majority of persons provided with a stoma.

In general terms, it may even be said that, up to the present time, no system exists specifically to resolve the problems posed by the emission of sound from an artificial anus, and the systems for the discharge and the deodorization of intestinal gases described hitherto in association with collecting bags for persons with a stoma do not in themselves make it possible to obtain a reduction in the noise emitted by the artificial anus to which these bags are applied.

Furthermore, even if certain persons have attempted to attach to these collecting bags devices which may possibly somewhat decrease noise, and which form part of certain known plugging systems, as stated hereinabove, this has in no way made it possible to provide users with a device reducing the noise emitted by an artificial anus, whether or not the persons provided with a stoma carry out irrigation, and at the same time ensuring good evacuation of excreta for all persons who have undergone enterostomy. A device for reducing the noise emitted by a stoma is acceptable only if it does not interfere with the free passage and collection of stool.

It has now been found that it is possible to achieve all these objectives by means of an original device which will be described in greater detail hereinafter, and which basically comprises an oblong body of open-cell porous material, sheathed in a casing of a material that does not adhere to the walls of the stoma and the upstream and downstream portions of which, in the direction of flow of stools and body fluid through the stoma, each comprises at least one opening adapted to allow passage of the intestinal gases emitted, the said oblong body being adapted to be inserted into the last portion of the intestine at the outlet thereof in the abdominal wall.

The object of the invention is, therefore, a device for reducing the noise emitted by an artificial anus, which basically comprises an oblong body of an open-cell porous material, sheathed in a casing of a material that does not adhere to the walls of the stoma and the upstream and downstream portions of which, in the direction of flow of steel and body fluid through the stoma, each comprises at least one aperture suited to allow passage of the intestinal gases emitted, the said oblong body being adapted to be inserted into the end portion of the intestine at the outlet thereof through the abdominal wall.

Such a device has been shown to be suited both to ensure expansion of the intestinal gases emitted and to maintain the intestinal walls constantly separated; it is by these two combined actions that it can abolish any noise emitted by the stoma. It has further been noted that this device is beneficial in preventing stenosis of the stoma.

The device according to the invention protects the patient from audible emissions until a stool is passed; this occurs normally and takes place after the removal of the device positioned in the stoma. The fact that this device can easily be removed either manually or even without outside intervention other than that of the passing of stool, according to the modes of embodiments, constitutes a further advantage.

According to another embodiment, this device can further contribute to deodorizing the intestinal gases emitted and, with this end in view, it has been proved very advantageous to provide the cells of the open-cell porous material with a charge of deodorizing material, such as activated charcoal.

Therefore, a further object of the invention is a device as described hereinabove and wherein at least a portion of the open-cell porous material contains a charge of absorbent material, such as activated charcoal.

This charge of absorbent material can be introduced into the cells by any means known to those skilled in the art, and can, if necessary, be secured therein by conventional means, notably by a suitable resin.

The invention is described hereinafter with reference to the figures of the appended drawings, which illustrate it and in which.

In the present context, the term "oblong body" (1) is used for any body having a symmetry axis of revolution and the maximum length of which is about 1 to 5 times the maximum diameter.

In practice, the greatest diameter of the oblong body can be from about 5 to 40 mm, whereas its length can, for example, be about 5 to 50 mm.

It should be noted, however, that to be effective it is not indispensable for this device to be perfectly cylindrical in shape. On the contrary, instead of a cylindrically shaped device, preference may be given to a substantially cylindrical device at least one of the ends of which is rounded such as that of FIG. 1, a substantially pyriform device such as that of FIG. 2, a substantially frusto-conical device having its large base connected by a rounded portion to the rest of the body, etc.

The skilled artisan is able to choose and select from all existing materials and substances those suited to the embodiment of a device according to this invention.

The open-cell porous body (2) can be made from any material of this type, such as open-cell polymer or elastomer foams, felts or fabrics, but open-cell polyurethane foams are particularly preferred.

The material for the casing (3) of this porous body can be any material ensuring good sliding on the intestinal walls, and particularly a natural or synthetic silicone rubber, or more generally any flexible elastomer, but this covering can also be made of a flexible gel essentially made from gelatin, glycerine and water, and which has the advantages of being bio-compatible and bio-degradable.

The device of the invention comprises at both ends thereof, not necessarily in the axis of the oblong body, but nevertheless at positions which must not be in direct contact with the intestinal walls, openings (such as perforations or slits (4) for example), of a size and in numbers suited for this purpose. In practice, perforations of about 1 to 4 mm in diameter, or even slits whose largest dimension is about 1 to 4 mm, are quite suitable.

The greater the number of openings the smaller should be the size thereof.

The device according to the invention can further comprise a member, such as a cord (5), suited to positioning it in the stoma and/or its recovery therefrom. Such a member is, however, provided more to reassure the patient, as it is quite unnecessary. The device described above is well inserted into the end of the intestine opening and remains there until the first stool is passed; this pushes it out, owing to the fact that all stoma are devoid of sphincters, which prevents any risk of the said device being drawn further into the intestine.

Figures 1, 2:
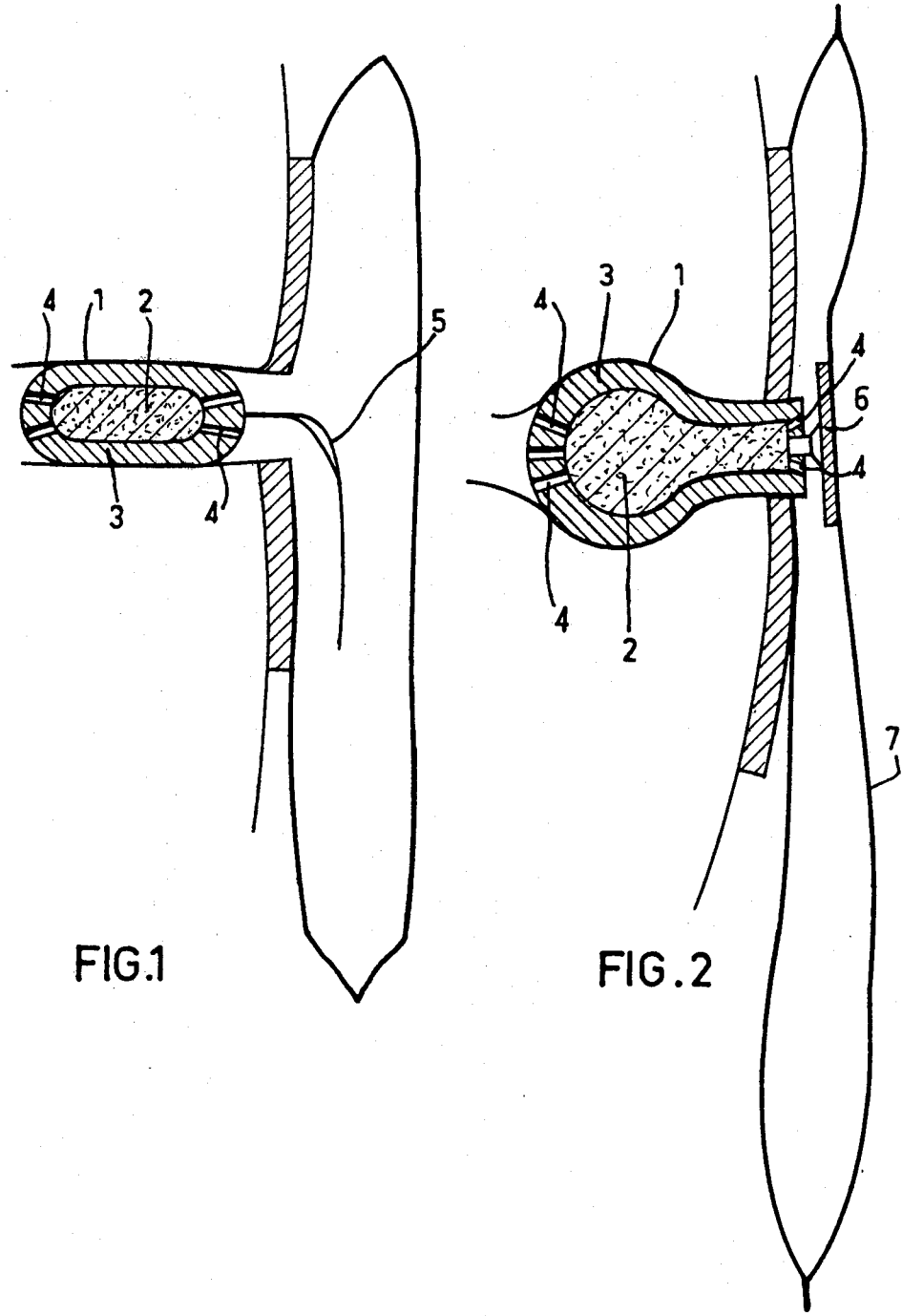
FIG. 1 is a diagrammatic cross-sectional view of a device according to the invention, positioned in a stoma to which a collecting bag is applied.
FIG. 2 is a diagrammatic cross-sectional view of another embodiment of this device, also positioned in a stoma provided with a collecting bag, and associated therewith.

However, according to the embodiment schematized in FIG. 2, the aforesaid oblong body has, at the downstream end thereof, a hard or semi-flexible member (6) forming a stem having the end opposite the oblong body flared into a disk secured to the inner surface of a collecting bag (7) opposite the opening thereof and which is applied to the outlet of the stoma and opposite said opening, whereby the device ejected into the said bag after stool passing can be, if so desired, reinserted by hand into the end portion of the intestine from which it will be again ejected when the next stool is passed.

Figures 3, 4:
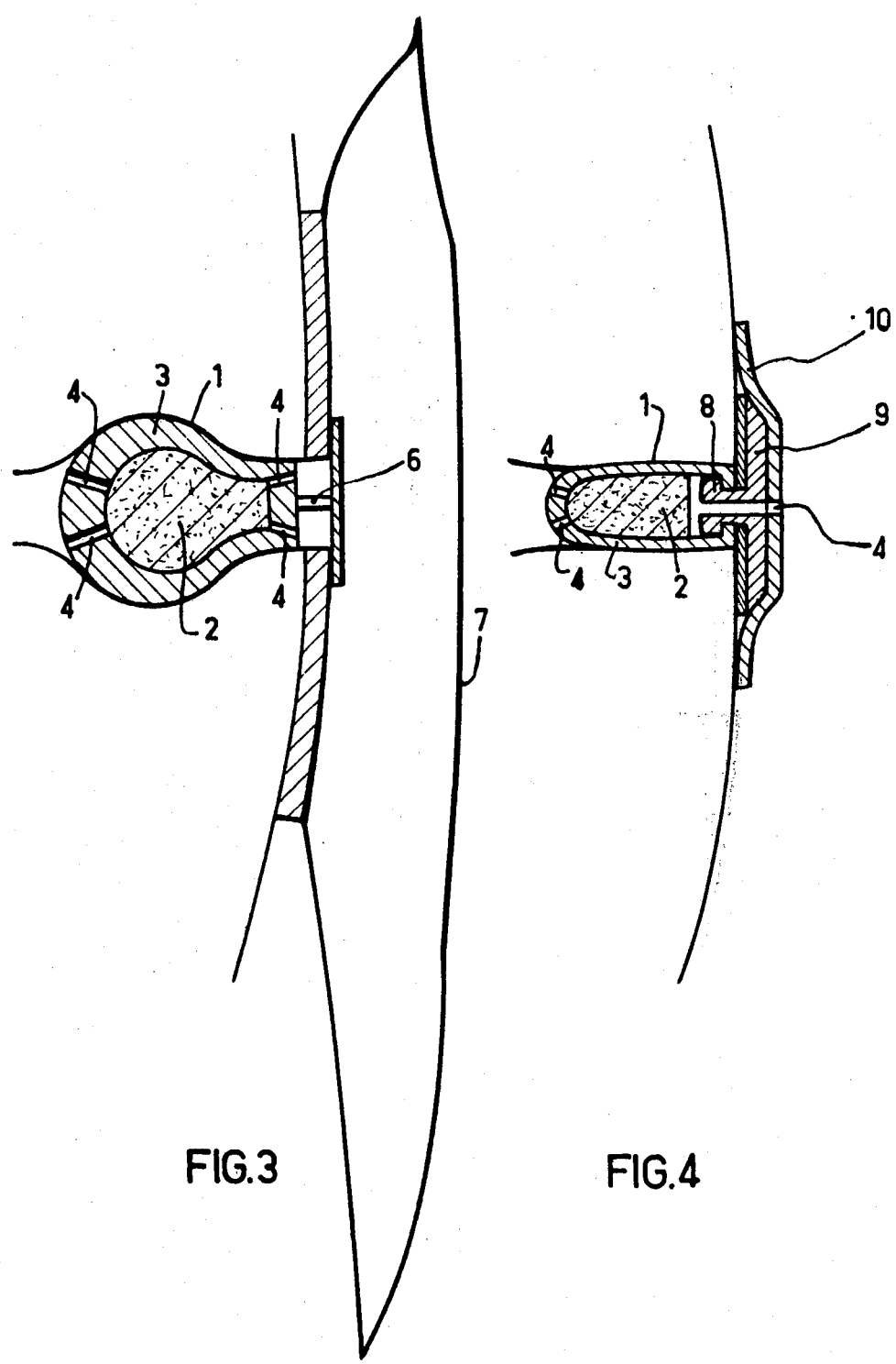
FIG. 3 is a diagrammatic cross-sectional view of another embodiment of the device of FIG. 2, in which an oblong body is secured to the inner forward portion of a collecting bag, and on the periphery of the opening thereof.
FIG. 4 is a diagrammatic cross-sectional view of another embodiment of the device according to the invention, wherein the oblong body is connected to an adhesive disk which can in turn be secured to the peri-orificial area of a stoma.

In the variant illustrated diagrammatically in FIG. 3, which has something in common with that of FIG. 2, the hard or semi-flexible member (6), instead of being secured to the wall of the collecting bag (7) opposite the opening thereof, is rigidly secured to the inner front portion of the collecting bag, on only one portion of the periphery of the opening of same, smaller than the half-periphery of this opening and preferably situated on the portion of the said opening that is the upper portion when the collecting bag is worn by the user.

In both these embodiments, security of the aforesaid member (6) on the one hand onto the oblong body (1) and on the other hand onto the inner surface of the collecting bag (7) can be obtained by any suitable means known to the skilled artisan, and particularly by bonding or by welding.

According to the embodiment schematized in FIG. 4, intended more particularly for persons carrying out irrigation, the casing (3) of the device of FIG. 1 comprises at the downstream end thereof an opening large enough to receive, preferably by ratchetting, a fixing member (8) having a symmetry axis of revolution adapted to be inserted into the downstream portion of the casing wherein a space is formed for this purpose and ending at the other extremity in a disk (9) of any size and thickness, adapted to bear upon the periphery of the stoma and further carrying, for this purpose, a suitable fixing means such as, for example, a flexible adhesive disk (10) which may have the form of a thick paste of the type commonly used to form joints around stomas; in this variant, the member (8) comprises an axial central channel emerging upstream adjacent to the open-cell porous body and downstream on the adhesive (10) which is either made of a porous material or comprises a suitable central opening. If so desired, this device can further comprise on the surface of the back disk shaped portion of the member (8) facing the stoma in the utilization position, a disk of flexible and soft material, such as cotton or felt, the centre of which is perforated to be positionable on member (8) against the disk-shaped portion thereof, and having a diameter smaller than that of the adhesive disk (10).

As a further embodiment (not shown) the device of FIG. 4 can comprise an attachment member (8) the portion of which that is situated outside the casing (3) where said member is inserted, has, in cross-section, substantially the profile of an archer's bow turned towards the remainder of the device, thus clearing around the stoma outlet a free volume in which can easily be housed the rim of stomas which are not flat. The casing (3) and the fixing member (8) can form a single part. This member (8) is then secured to the patient's abdomen by means, for example, of a ring of double-faced adhesive material situated adjacent to the periphery of member (8) with a bow-shaped profile on the side turned towards the abdomen in the position of use. The member (8) thus constituted obviously has a central axial channel formed right through it.

Each of the aforesaid embodiments can again be improved, if so desired, either by the introduction into the open-cells of the porous material (2) of a charge of deodorizing material such as, for example, activated charcoal, this charge of odour-absorbing material can being simply deposited in at least some of the cells of the porous material or being secured to the walls thereof, for example, by a suitable resin, or by replacing at least part of the porous material (2) by such an absorbant material which, in the form of fibers, granules or the like, constitutes the porous material.

The invention is illustrated more concretely in the following working examples, which in no way limit it.

EXAMPLE 1

An oblong body having an outer diameter of 12 mm and a maximum length of 20 mm was formed by enclosing a polyurethane foam of suitable shape and size in a capsule formed by means of a resilient gel obtained after heating a mixture of 50% by weight water, 25% by weight gelatin and 25% by weight glycerine for 15 minutes at 120° C., and cooling it, and in which a 4 mm diameter perforation has been formed, at each end of the rounded ends of the oblong body and substantially in the axis thereof, which causes the open-cell porous material to communicate with the exterior.

Although the material of the capsules so formed is not particularly water-soluble, it is broken down by bacterial action after a certain length of time in an aqueous medium. Such breakdown, however, takes sufficiently long for it not to adversely affect the satisfactory operation of the device in the application in question.

After being introduced into the end of the intestine of a patient who has undergone enterostomy, and the application of a collecting bag to the stoma, it was observed that no more noises could be heard such as were audible at irregular intervals from the same patient when they wore a collecting bag of the same type but without having previously inserted into the stoma a device according to the invention.

EXAMPLE 2

A device was produced corresponding to the one of example 1, except that it comprised, on the outer side of the stoma, not one single 4 mm diameter perforation but three 1.5 mm perforations offset from each other; furthermore, at this same end of the device, there is provided a substantially stem shaped member the other end of which is flared and secured by bonding onto the inner wall of a collecting bag for persons who have undergone enterostomy and opposite the opening formed in this bag.

Experimentation with this device under the same conditions also lead to the same conclusions as those given for example 1. In addition, this device has the advantage of being manually reinsertable into the stoma after the passing of a stool.

EXAMPLE 3

A post-irrigation device was produced that could be used without a collecting bag and having a structure corresponding to the diagram of FIG. 4. The oblong body of polyurethane foam charged with activated charcoal was enclosed in a rubber casing extending beyond the porous body and disposed to be able to ratch onto a polyethylene fixing member (reference 8 in FIG. 4) having a 1.5 mm diameter axial central channel. The rubber seal had three 1.5 mm diameter openings at the upstream end thereof, slightly offset with regard to the axis of symmetry. A cotton disk with a central perforation was inserted into the aforesaid fixing member before ratching onto the latter, the casing of the oblong body and a disk of a single face adhesive material, comprising an approximately 1.5 mm diameter central opening coaxial with the aforesaid channel, and having a diameter greater than that of the aforesaid cotton disk, was applied to the aforesaid fixing member and bore an annular protective material covering the adhesive-free portion. After having removed this protective material, this device was applied by adhesive onto the peri-orificial portion of the stoma of a patient, in which penetrated the casing containing the porous material. The cotton disk (which can be replaced by a felt one) ensures soft contact with the edges of the orifice. The patient wearing this device observed no untimely audible sound and no emission of smell.

I claim:
1. A combination of a collecting bag and a reusable device for reducing noise emitted by an artificial anus;
   the device comprising a body of open-cell porous material sheathed in an outer casing that does not adhere to stoma walls with which it is adapted to make direct contact;
   the casing of the body having upstream and downstream ends (with respect to flow of stool and body fluid through the stoma), each of which comprises a through opening in communication with the porous material and suited for passing emitted intestinal gases;
   said device being adapted to be inserted into an accessible intestine end portion, to be displaced into the collecting bag by stool and to be reinserted into the accessible intestine end portion thereafter.

2. A combination according to claim 1 wherein the downstream end of the casing has a disk attached thereto, and the disk is secured to an inner surface of said collecting bag.

3. A combination according to claim 2 wherein the collecting bag has an inlet opening, and the inner surface is that which is opposite to and facing the inlet opening.

4. A combination according to claim 2 wherein the collecting bag has a front portion with an inlet opening therein, and the inner surface is a portion of that which surrounds the inlet opening.

5. A combination according to claim 1 wherein the porous material is open-cell polyurethane.

6. A combination according to one of claims 1 to 5 wherein the casing of the porous body is made of flexible elastomer.

7. A combination according to one of claims 1 to 5 wherein the casing of the porous body is made of flexible gel.

8. A combination according to claim 7 wherein the flexible gel is that of gelatin, glycerine and water.

9. A combination according to one of claims 1 to 5 wherein each opening in the casing ends is a perforation or slit, the largest dimension of which is from about 1 to about 4 mm.

* * * * *